United States Patent [19]
Yamada et al.

[11] Patent Number: 6,087,104
[45] Date of Patent: Jul. 11, 2000

[54] **OLIGONUCLEOTIDES FOR DETECTION OF *BACILLUS CEREUS* GROUP BACTERIA HARMFUL TO MAMMALS, AND METHOD OF DETECTION WITH THE OLIGONUCLEOTIDES**

[75] Inventors: Shoichi Yamada, Tokyo, Japan; Kasthuri Venkateswaran, Arcadia, Calif.; Eiji Ohashi, Tokyo, Japan

[73] Assignee: Nippon Suisan Kaisha, Ltd., Tokyo, Japan

[21] Appl. No.: 09/046,578

[22] Filed: Mar. 24, 1998

[30]       Foreign Application Priority Data

| Mar. 24, 1997 | [JP] | Japan | 9-069900 |
| Apr. 21, 1997 | [JP] | Japan | 9-102843 |
| Sep. 29, 1997 | [JP] | Japan | 9-264057 |
| Sep. 29, 1997 | [JP] | Japan | 9-264058 |
| Sep. 29, 1997 | [JP] | Japan | 9-264059 |

[51] Int. Cl.$^7$ .............. C12Q 1/68; C12P 19/34; C07H 21/02; C07H 21/04
[52] U.S. Cl. .............. 435/6; 435/91.2; 435/91.5; 536/23.1; 536/23.2; 536/23.7; 536/24.32; 536/24.33
[58] Field of Search .............. 435/6, 91.1, 91.2, 435/91.5; 536/23.1, 23.2, 23.7, 24.3, 24.32, 24.33

[56]            References Cited

PUBLICATIONS

Abdel–Hameed, A. et al. Studies on *Bacillus thuringiensis* strains isolated from Swedish soils: insect toxicity and production of *B. cereus*–diarrhoeal–type enterotoxin, World J. Microbiology & Biotechnology vol. 10 (1994), p406–409.

González, Jr., J.M. et al. Transfer of *Bacillus thuringiensis* plasmids coding for δ–endotoxin among strains of *B. thuringiensis* and *B. cereus*, Proc. pro. Natl. Acad. Sci. USA, vol. 79 (1982), p6951–6955.

Agata, N. et al. The bceT gene of *Bacillus cereus* encodes an enterotoxic protein, Microbiology 141 (1995), p983–988.

Yamamoto, S. et al. PCR Amplification and Direct Sequencing of gyrB Genes with Universal Primers and Their Application to the Detection and Taxonomic Analysis of *Pseudomonas putida* Strains, Applied & Environmental Microbiology, Mar. 1995, p1104–1109.

Beecher, D.J. et al. Identification and Analysis of the Antigens Detected by Two Commercial *Bacillus cereus* Diarrheal Enterotoxin Immunoassay Kits, Applied & Environmental Microbiology, Dec. 1994, p4614–4616.

Granum, P.E. et al. A survey of bacterial toxins involved in food poisoning: a suggestion for bacterial food poisoning toxin nomenclature, International Journal of Food Microbiology 28 (1995), p129–144.

Uchida, I. et al. Association of the Encapsulation of *Bacillus anthracis* with a 60 Megadalton Plasmid, Journal of General Microbiology 131 (1985), p363–367.

Saiki, R.K. et al. Primer–Directed Enzymatic Amplification of DNA with a Thermostable DNA Polymerase, Science vol. 239 (1988), p487–491.

Patra, G. et al. Isolation of a specific chromosomic DNA sequence of *Bacillus anthracis* and its possible use in diagnosis. FEMS Immuno. Med. Micro. 15:223–231, 1996.

*Primary Examiner*—Carla J. Myers
*Assistant Examiner*—Diana Johannsen
*Attorney, Agent, or Firm*—Armstrong, Westerman, Hattori, McLeland & Naughton

[57]            ABSTRACT

A method of detection is provided that permits differentiation of each of *Bacillus cereus, Bacillus thuringiensis*, and *Bacillus anthracis* from other microorganisms, using oligonucleotide primers for amplification of the target nucleotide sequences characteristic to *Bacillus cereus, Bacillus thuringiensis*, and *Bacillus anthracis*, consisting of the oligonucleotide (A) having a nucleotide sequence obtained from SEQ ID NO:1 and containing at least one site that can amplify a nucleotide sequence characteristic to *Bacillus cereus*, the oligonucleotide (B) having a nucleotide sequence obtained from SEQ ID NO:3 and containing at least one site that can amplify a nucleotide sequence characteristic to *Bacillus thuringiensis*, and the oligonucleotide (C) having a nucleotide sequence obtained from SEQ ID NO:5 and containing at least one site that can amplify a nucleotide sequence characteristic to *Bacillus anthracis*. Also provided are a method of detection of *Bacillus cereus, Bacillus thuringiensis*, and *Bacillus anthracis* by polymerase chain reaction (PCR) using a primer specific to the DNA gyrase sub-unit B (gyrB) gene and a method of detection of *Bacillus cereus, Bacillus thuringiensis*, and *Bacillus anthracis* in a sample by differentiation on the genetic level.

16 Claims, No Drawings

OLIGONUCLEOTIDES FOR DETECTION OF *BACILLUS CEREUS* GROUP BACTERIA HARMFUL TO MAMMALS, AND METHOD OF DETECTION WITH THE OLIGONUCLEOTIDES

FIELD OF THE INVENTION

This invention relates to oligonucleotides for detection of *Bacillus cereus* group bacteria harmful to mammals, and in more detail, it relates to oligonucleotide primers for amplification of the target nucleotide sequence characteristic to *Bacillus cereus, Bacillus thuringiensis*, or *Bacillus anthracis*.

This invention also relates to detection of *Bacillus cereus, Bacillus thuringiensis*, and *Bacillus anthracis* based on the polymerase chain reaction (PCR) using DNA gyrase subunit B (gyrB) gene-specific primers.

In addition, this invention relates to the method of detection by differentiation of *Bacillus cereus, Bacillus thuringiensis*, and *Bacillus anthracis* in a sample on the genetic level.

PRIOR ART

*Bacillus cereus* occurs widely in the natural world, being found in soil and in food, and is known to be a food-borne human pathogen causing emesis or diarrhea. *Bacillus cereus* is a Gram-positive bacillus and heat-resistant because it is a spore forming. In Japan, emesis-type food poisoning tends to develop after ingestion of rice or noodle, while diarrhea-type food poisoning tends to develop after ingestion of meat, soup, or other food.

The latency of the emesis-type food poisoning is 1 to 5 hours while that of the diarrhea-type one is 8 to 16 hours. In the former case the toxin produced within the food is responsible for poisoning, while in the latter case enterotoxin produced as a result of proliferation of the bacteria in the intestine is responsible. The bacteria not only cause food poisoning but also are causative of putrefaction and deterioration of food along with their proliferation.

*Bacillus thuringiensis* is known to occur widely in the natural world, being found in soil and in food. *Bacillus thuringiensis* is a Gram-positive bacillus and heat-resistant because it is a spore forming. *Bacillus thuringiensis* is also known to produce insecticidal protein.

*Bacillus anthracis* is a Gram-positive bacillus and heat-resistant because it is a spore forming. *Bacillus anthracis* is clinically very important because it is a pathogen of anthrax, a zoonotic infection.

For isolation and identification of *Bacillus cereus, Bacillus thuringiensis*, and *Bacillus anthracis*, normally Mannitol Egg-yolk Polymyxin (MYP) agar medium or a selective medium prepared by addition of egg-yolk solution to NaCl Glycine Kim and Goepfert (NGKG) agar medium is used, and the colony showing egg-yolk reaction is considered positive. In addition it should be confirmed that the colony is positive in nitrate reduction, citrate utilization, hydrolysis of gelatin, VP reaction, and acid from glucose, and negative in acid from mannitol, arabinose, and xylose.

The results of the above-mentioned confirmation tests are the same for *Bacillus cereus, Bacillus thuringiensis, Bacillus anthracis*, and *Bacillus mycoides* which are related to each other.

Differentiation of *Bacillus cereus* from *Bacillus anthracis* is based on the fact that the former is mostly motile whereas the latter is not motile and gamma-phage susceptible, and that the former causes hemolyis of sheep blood cells and decomposition of tyrosine whereas the latter does not.

*Bacillus cereus* or *Bacillus thuringiensis* can be differentiated from *Bacillus mycoides* based on the fact that *Bacillus mycoides* is not motile, causes hemolysis, does not decompose tyrosine, and indicates rhizoid growth. These confirmation tests take a lot of time and require much labor before judgment is made.

*Bacillus thuringiensis*, a related species, is differentiated from *Bacillus cereus* based on the fact that the former produces insecticidal protein, though they share the same biochemical properties. According to the current taxonomy, the bacteria with microscopically confirmed insecticidal protein are classified as *Bacillus thuringiensis*, though these two species cannot be differentiated clearly based on the serotype. There is a report that some strains of *Bacillus thuringiensis* produce enterotoxin similar to that produced by *Bacillus cereus* [World J. Microbiol. Biotechnol. 10 (1994) p406–409]. Based on the report that plasmid may be transferred between *Bacillus cereus* and *Bacillus thuringiensis* [Proc. Natl. Acad. Sci. USA 79 (1982) p6951–6955], it is probable that the plasmid encoding the insecticidal protein has been transferred into the strains originally belonging to *Bacillus cereus* under some influence. Therefore some of the strains classified as *Bacillus thuringiensis* according to the current taxonomy based on the presence of the insecticidal protein may be causative of food poisoning. *Bacillus thuringiensis* is sprayed over soil as a biological control agent for insects, and thus apprehension is felt about its safety.

Under these circumstances it has become necessary to differentiate *Bacillus cereus* from *Bacillus thuringiensis* from a viewpoint other than the insecticidal protein. As for the toxin of *Bacillus cereus*, the diarrhea-causing enterotoxin was cloned and its base sequence was determined [Microbiology, 141 (1995), p983–988J. However it still remains unknown whether this is the sole diarrhea-causing enterotoxin. A kit for detection of this enterotoxin is commercially available but not necessarily rated high because all of the enterotoxins of *Bacillus cereus* have not yet been clarified [Appl. Environ. Microbiol., 60 (1994), p4614–4616]. There is a report that the emesis-causing toxin is a cyclic peptide [Int. J. Food Microbiology 28 (1995), p129–144]. Some strains of *Bacillus cereus* do not produce any toxin, and therefore detection of *Bacillus cereus* based solely on the presence of toxin is not always reliable.

The 16s rRNA sequences used for analysis on the genetic level reveal homology of 99% or more between *Bacillus cereus* and *Bacillus anthracis*, thereby being difficult to be used as an index for identification.

PROBLEM TO BE SOLVED BY THE INVENTION

The so-called *Bacillus cereus* group includes *Bacillus thuringiensis, Bacillus anthracis*, and *Bacillus mycoides* in addition to *Bacillus cereus*. From the viewpoint of hazard for man and cattle, *Bacillus cereus, Bacillus thuringiensis*, and *Bacillus anthracis* are unfavorable because these produce toxin, whereas *Bacillus mycoides* does not produce toxin and may be grouped differently from the former three in respect of the safety. Thus it may b e meaningful that *Bacillus cereus, Bacillus thuringiensis*, and *Bacillus anthracis* can be detected as mentioned above.

For example, when cereus group bacteria causative of food poisoning are to be detected in food, safety will be assured firmly if not only *cereus*-specific primer but also thuringiensis- and anthracis-specific primers are used for detection in consideration of the possible hazard of these three species.

The purpose of this invention is to provide a method for detection with which each of Bacillus cereus, Bacillus thuringiensis, and Bacillus anthracis can be differentiated from other microorganisms.

The purpose of this invention is to provide a method for detection of the Bacillus cereus-specific 365bp gyrB gene fragment from bacterial cells without DNA extraction by PCR using the Bacillus cereus-specific primer.

The purpose of this invention is to provide a method for detection of the Bacillus thuringiensis-specific 367bp gyrb gene fragment from bacterial cells without DNA extraction by PCR using the Bacillus thuringiensis-specific primer.

The purpose of this invention is to provide a method for detection of the Bacillus anthracis-specific 245bp gyrB gene fragment in bacterial cells without DNA extraction by PCR using the Bacillus anthracis-specific primer.

In addition, the purpose of this invention is to provide a method for detection of Bacillus cereus, Bacillus thuringiensis, and Bacillus anthracis, which belong to the Bacillus cereus group, in a sample based on differentiation on the genetic level.

MEANS TO SOLVE THE PROBLEM

The gist of this invention is at least one oligonucleotide selected among the group consisting of the oligonucleotide (A) having a nucleotide sequence obtained from SEQ ID NO:1 of the SEQUENCE LISTING and containing at least one site capable of amplifying the nucleotide sequence characteristic to Bacillus cereus, the oligonucleotide (B) having a nucleotide sequence obtained from SEQ ID NO:3 and containing at least one site capable of amplifying the nucleotide sequence characteristic to Bacillus thuringiensis, and the oligonucleotide (C) having a nucleotide sequence obtained from SEQ ID NO:5 and containing at least one site capable of amplifying the nucleotide sequence characteristic to Bacillus anthracis.

The above-mentioned oligonucleotide (A) has no nucleotide sequence obtained from SEQ ID NO:3 or from SEQ ID NO:5, the above-mentioned oligonucleotide (B) has no nucleotide sequence obtained from SEQ ID NO:1 or from SEQ ID NO:5, and the above-mentioned oligonucleotide (C) has no nucleotide sequence obtained from SEQ ID NO:1 or from SEQ ID NO:3; therefore the gist of this invention is at least one oligonucleotide selected among the group consisting of the oligonucleotide (A) having a nucleotide sequence obtained from SEQ ID NO:1, not having the nucleotide sequence obtained from SEQ ID NO:3 or from SEQ ID NO:5, and containing at least one site capable of amplifying the nucleotide sequence characteristic to Bacillus cereus, the oligonucleotide (B) having a nucleotide sequence obtain ed from SEQ ID NO:3, not having the nucleotide sequence obtained from SEQ ID NO:1 or from SEQ ID NO:5, and containing at least one site capable of amplifying the nucleotide sequence characteristic to Bacillus thuringiensis, and the oligonucleotide (C) having a nucleotide sequence obtained from SEQ ID NO:5, not having the nucleotide sequence obtained from SEQ ID NO:1 or from SEQ ID NO:3, and containing at least one site capable of amplifying the nucleotide sequence characteristic to Bacillus anthracis.

The above-mentioned oligonucleotide (A) is the oligonucleotide not having the site that can amplify the nucleotide sequence derived from Bacillus thuringiensis or from Bacillus anthracis, the above-mentioned oligonucleotide (B) is the oligonucleotide not having the site that can amplify the nucleotide sequence derived from Bacillus cereus or from Bacillus anthracis, and the above-mentioned oligonucleotide (C) is the oligonucleotide not having the site that can amplify the nucleotide sequence derived from Bacillus cereus or from Bacillus thuringiensis; therefore the gist of this invention is at least one oligonucleotide selected among the group consisting of the oligonucleotide (A) having the nucleotide sequence obtained from SEQ ID NO:1, not having the site that can amplify the nucleotide sequence derived from Bacillus thuringiensis or from Bacillus anthracis, and containing at least one site capable of amplifying the nucleotide sequence characteristic to Bacillus cereus, the oligonucleotide (B) having the nucleotide sequence obtained from SEQ ID NO:3, not having the site that can amplify the nucleotide sequence derived from Bacillus cereus or from Bacillus anthracis, and containing at least one site capable of amplifying the nucleotide sequence characteristic to Bacillus thuringiensis, and the oligonucleotide (C) having a nucleotide sequence obtained from SEQ ID NO:5, not having the site that can amplify the nucleotide sequence derived from Bacillus cereus or from Bacillus thuringiensis, and containing at least one site capable of amplifying the nucleotide sequence characteristic to Bacillus anthracis.

In the concrete, the above-mentioned oligonucleotide (A) is the oligonucleotide containing the nucleotide sequence of SEQ ID NO:7 or of SEQ ID NO:8, the above-mentioned oligonucleotide (B) is the oligonucleotide containing the nucleotide sequence of SEQ ID NO:9 or of SEQ ID NO:10, and the above-mentioned oligonucleotide (C) is the oligonucleotide containing the nucleotide sequence of SEQ ID NO:11 or of SEQ ID NO:12; desirably, the above-mentioned oligonucleotide (A) is a primer set consisting of the oligonucleotide ($a_1$) containing the nucleotide sequence of SEQ ID NO:7 and the oligonucleotide ($a_2$) containing the nucleotide sequence of SEQ ID NO:8, the above-mentioned oligonucleotide (B) is a primer set consisting of the oligonucleotide ($b_1$) containing the nucleotide sequence of SEQ ID NO:9 and the oligonucleotide ($b_2$) containing the nucleotide sequence of SEQ ID NO:10, and the above-mentioned oligonucleotide (C) is a primer set consisting of the oligonucleotide ($c_1$) containing the nucleotide sequence of SEQ ID NO:11 and the oligonucleotide ($c_2$) containing the nucleotide sequence of SEQ ID NO:12.

In addition, the gist of this invention is the method for detection based on differentiation of Bacillus cereus, Bacillus thuringiensis, and Bacillus anthracis on the genetic level, using the above-mentioned oligonucleotide (A), the above-mentioned oligonucleotide (B), or the above-mentioned oligonucleotide (C) for selective amplification of the target DNA gyrase sub-unit B (gyrB) gene sequence specific to respective species, and taking respective gyrB genes as the index.

The gist of this invention is the method for detection of Bacillus thuringiensis and Bacillus anthracis based on differentiation on the genetic level, characterized in that a primer set consisting of two different above-mentioned oligonucleotides (A) as the above-mentioned oligonucleotide (A), or a primer set consisting of two different above-mentioned oligonucleotides (B) as the above-mentioned oligonucleotide (B), or a primer set consisting of two different above-mentioned oligonucleotides (C) as the above-mentioned oligonucleotide (C) is used for selective amplification of the target DNA gyrase sub-unit B (gyrB) gene sequence specific to respective species in a sample, and the presence or absence of the gyrB specific to Bacillus cereus, Bacillus thuringiensis, or Bacillus anthracis is determined.

The gist of this invention is the method for detection of *Bacillus thuringiensis* and *Bacillus anthracis* based on differentiation on the genetic level, characterized in that a primer set consisting of the oligonucleotide ($a_1$) containing the nucleotide sequence of SEQ ID NO:7 and the oligonucleotide ($a_2$) containing the nucleotide sequence of Sequence No.8 as the above-mentioned oligonucleotide (A), or a primer set consisting of the oligonucleotide ($b_1$) containing the nucleotide sequence of SEQ ID NO:9 and the oligonucleotide ($b_2$) containing the nucleotide sequence of SEQ ID NO:10 as the above-mentioned oligonucleotides (B), or a primer set consisting of the oligonucleotide ($c_1$) containing the nucleotide sequence of SEQ ID NO:11 and the oligonucleotide ($c_2$) containing the nucleotide sequence of SEQ ID NO:12 as the above-mentioned oligonucleotide (C) is used for selective amplification of the target DNA gyrase sub-unit B (gyrB) gene sequence specific to respective species in a sample, and the presence or absence of the gyrB specific to *Bacillus cereus, Bacillus thuringiensis*, or *Bacillus anthracis* is determined.

The amino acid sequence of SEQ ID NO:2 is the amino acid sequence that the above-mentioned nucleotide sequence of SEQ ID NO:1 encodes, the amino acid sequence of SEQ ID NO:4 is the amino acid sequence that the above-mentioned nucleotide sequence of SEQ ID NO:3 encodes, and the amino acid sequence of SEQ ID NO:6 is the amino acid sequence that the above-mentioned nucleotide sequence of SEQ ID NO:5 encodes.

MODE FOR CARRYING OUT THE INVENTION

This invention is based on the oligonucleotide primers that are useful for determination of the presence or absence of the target nucleotide sequences specific to *Bacillus cereus, Bacillus thuringiensis*, and *Bacillus anthracis*, and the method for making the determination includes not only the gene amplification method using PCR, but also the use of the primers as probes in the prior art Southern hybridization method.

In this invention, "primers" means oligonucleotides with the designed or biologically produced specific nucleotide sequence that permits hybridization to the target nucleotide sequence. Primers can hybridize to the complete target nucleotide sequence produced by extension with polymerase or a similar enzyme. Primers are utilized in nucleic acid amplification techniques, for example in PCR and strand displacement amplification (SDA). Certain primers, especially those useful in the SDA technique, contain, in addition to the sequence capable of hybridizing to the target nucleic acid, the sequence that restriction endonuclease recognizes, and a sequence required for polymerase or other enzymes for continuation of polymerase-like activity to direct the initiation of its template-specific oligonucleotide synthesis.

In this invention, "hybridization" is a process where under predetermined reaction conditions, partially or completely complementary nucleic acid strands, standing opposite to each other in an anti-parallel way, form a double-stranded nucleic acid through specific and stable hydrogen bonds.

The oligonucleotide primers for amplification of the target nucleotide sequences characteristic to *Bacillus cereus, Bacillus thuringiensis*, and *Bacillus anthracis* in this invention contain favorably SEQ ID NO:7 and SEQ ID NO:8 for *Bacillus cereus*, SEQ ID NO:9 and SEQ ID NO:10 for *Bacillus thuringiensis*, and SEQ ID NO:11 and SEQ ID NO:12 for *Bacillus anthracis*, and are used as a primer set in the method for determination of the presence or absence of the target nucleotide sequence characteristic to *Bacillus cereus, Bacillus thuringiensis*, or *Bacillus anthracis*.

The *Bacillus cereus*-specific primer, the *Bacillus thuringiensis*-specific primer, and the *Bacillus anthracis*-specific primer enable to detect the *Bacillus cereus*-specific 365bp gyrB gene fragment, the *Bacillus thuringiensis*-specific 368bp gyrB gene fragment, and the *Bacillus anthracis*-specific 245bp gyrb gene fragment, respectively, from bacterial cells with the PCR method without DNA extraction. The primers in this invention are specific to the gyrB gene sequence of *Bacillus cereus*. The probe is specific to the internal consensus sequence within the primer-amplification product.

In the following is explained the method for production of primer sets consisting of oligonucleotides containing the nucleotide sequences of SEQ ID NO:7 and SEQ ID NO:8 for *Bacillus cereus*, those of SEQ ID NO:9 and SEQ ID NO:10 for *Bacillus thuringiensis*, and those of SEQ ID NO:11 and SEQ ID NO:12 for *Bacillus anthracis*.

As a highly specific probe is used the gyrB gene that encodes the B sub-unit protein of DNA gyrase (topoisomerase π).

A method has been reported for detection and classification of *Pseudomonas putida* using the universal primers which sequenced directly the gyrB gene [Appl. Environ. Microbiol., 61 (1995), p1104–1109]. These universal primers are commonly usable in various Gram-positive and Gram-negative bacteria, and a portion of gyrB gene was amplified with the PCR method.

With these known primers, the base sequence of *Bacillus cereus* JCM2152, *Bacillus thuringiensis* IAM12077, and *Bacillus anthracis* Pasteur no. 2-H was determined [Journal of General Microbiology, 131 (1985), p363].

In addition, the PCR primers that can amplify and identify only the gyrB gene of *Bacillus cereus* were prepared. To know the sensitivity of these *Bacillus cereus*-specific primers, we have checked about 15 strains of *Bacillus cereus, Bacillus thuringiensis, Bacillus anthracis, Bacillus mycoides, Bacillus subtilis, Bacillus brevis, Escherichia coli, Salmonella, Staphylococcus aureus*, and *Vibrio parahaemolyticus*.

Yamamoto and Harayama [Appl. Environ. Microbiol., 61 (1995), p1104–1109] and others prepared PCR primers that amplify a portion of the gyrB gene from 2 sites where the DNA gyrase B sub-unit was conserved. With these primers, about 1.2 kb size of the gyrB gene fragments were amplified from various bacteria.

The 1.2 kb gyrB gene fragments amplified from *Bacillus cereus* JCM2152, *Bacillus thuringiensis* IAM12077, or *Bacillus anthracis* Pasteur no. 2-H were cloned in appropriate vector by conventional recombinant methods (Sambrook et al., Molecular cloning: a laboratory manual, $2^{nd}$ ed., Cold Spring Harbour, New York. 1989).

A preferred vector is pGEMzf(+), though any standard vector that has been appropriately chosen may be used.

For preparation of effective primers, the 1.2 kb gyrB gene fragments amplified by the PCR method from *Bacillus cereus, Bacillus thuringiensis*, and *Bacillus anthracis* were cloned in pGEMzf(+), and the sequence of the gyrB gene regions was determined by conventional methods using a DNA sequencer.

For the sequencing of the gyrB gene, the sequence of 5' and 3' regions of the amplified fragments were sequenced with the UP-1S and UP-2Sr primers [Yamamoto and Harayama, Appl. Environ. Microbiol., 61 (1995), p1104–1109]. In this case the base sequence that can be determined with these primers is limited, so that new primers were prepared based on the sequence determined for further determination of base sequence of other regions. The base sequence of the gyrB gene of *Bacillus cereus* JCM2152, that of *Bacillus thuringiensis*, and that of *Bacillus anthracis* Pasteur no. 2-H are shown in SEQ ID NO:1, SEQ ID NO:3, and SEQ ID NO:5, respectively.

The information of the base sequence was then used to prepare the primer of 21 (~24 )mer that can detect and identify *Bacillus cereus* from other bacteria. This primer is oligonucleotides having the nucleotide sequences of SEQ ID NO:7 and SEQ ID NO:8, and can be used as a primer set.

These novel primers are useful in the known PCR assays [Saikiet al., Science 239 (1988), p487–491]. These primers are used for amplification of the target DNA contained in the sample.

The detection step following the amplification step may be carried out by any means as far as it is effective for detecting DNA, such as agarose gel electrophoresis followed by staining with ethidium bromide.

The target DNA serves as a template. The template DNA in the sample is amplified as follows: the primer is bound to the complementary region of the template, and DNA is extended from the binding site by using the template as a template. The extended DNA serves as a template of the primer. This process proceeds by repeating the cycle consisting of denaturing of DNA, annealing of the primer with the template, and extension of the primer with DNA polymerase (e.g. Taq polymerase), until the double-stranded DNA of a certain length has been amplified to the detectable quantity when two sets of primers are used.

However, if the template DNA does not contain any sequence complementary to the primer, the double-stranded DNA of a certain length will not be produced, and thus it can be concluded that there is no target template in the sample. Namely, the presence of the target bacteria in the sample can be excluded.

The primer set <BC1 (SEQ ID NO:7), BC2 (SEQ ID NO:8)> amplifies the sequence of a 365 bp fragment of the gyrB gene. In 15 strains of *Bacillus cereus* obtained from the JCM, IAM, IFO, and ATCC collections, the presence of the amplified fragment of 365 bp was confirmed.

The presence of the amplified fragment could not be confirmed in *Bacillus thuringiensis, Bacillus anthracis*, or *Bacillus mycoides*, which show biochemical properties very similar to those of *Bacillus cereus*. The amplified fragment could not be found in *Bacillus subtilis* or *Bacillus brevis*, both belonging to the same genus Bacillus. These findings demonstrate that the primer of this invention is specific to *Bacillus cereus* and thus can be used for detection of the food-borne pathogen.

The gyrB gene was found to be present also in the type strains of *Escherichia coli*, Salmonella, *Staphylococcus aureus*, and *Vibrio parahaemolyticus*, but the presence of the amplified fragment of 365 bp specific to *Bacillus cereus* was not confirmed.

In some strains of *Bacillus cereus*, the band at 365 bp could not be detected by electrophoresis after PCR even when the *Bacillus cereus*-specific primer was used.

With these strains, 21–24 mer primers specific respectively to *Bacillus thuringiensis* and *Bacillus anthracis* were prepared newly taking the gyrB gene as the index. The *Bacillus thuringiensis*-specific primer is an oligonucleotide having the nucleotide sequences of SEQ ID NO:9 and SEQ ID NO:10, while the *Bacillus anthracis*-specific primer is an oligonucleotide having the nucleotide sequences of SEQ ID NO:11 and SEQ ID NO:12. By staining with ethidium bromide after PCR and gel electrophoresis, the bands at 368 bp and 245 bp can be detected for *Bacillus thuringiensis* and *Bacillus anthracis*, respectively.

The amplified fragment of 368 bp was not detected in *Bacillus cereus, Bacillus anthracis*, or *Bacillus mycoides*, which have biochemical properties very similar to those of *Bacillus thuringiensis*. These findings demonstrate that the primer of this invention is specific to *Bacillus thuringiensis* and thus can be used for detection of the food-borne pathogen.

The amplified fragment of 245 bp was not detected in *Bacillus cereus, Bacillus thuringiensis*, or *Bacillus mycoides*, which have biochemical properties very similar to those of *Bacillus anthracis*. These findings demonstrate that the primer of this invention is specific to *Bacillus anthracis* and thus can be used for detectioon of the food-borne pathogen The *Bacillus cereus* strains that could not be detected with the *Bacillus cereus*-specific primer were subjected to PCR with the *Bacillus thuringiensis*- or *Bacillus anthracis*-specific primer: the strains could be detected with either of the primers. That is, *Bacillus cereus, Bacillus thuringiensis*, and *Bacillus anthracis* could be differentiated on the genetic level by taking the gyrB gene as the index. It will be very meaningful that *Bacillus cereus, Bacillus thuringiensis*, and *Bacillus anthracis* can be detected.

EXAMPLES

The detail of the present invention is illustrated in the following Examples. The present invention is not limited at all by these Examples.

Example 1

The primer set <BC1 (SEQ ID NO:7), BC2 (SEQ ID NO:8)> amplifies the 365 bp gyrB gene fragment. The sensitivity of this primer set was checked about 15 strains of *Bacillus cereus, Bacillus thuringiensis, Bacillus anthracis, Bacillus mycoides, Bacillus subtilis, Bacillus brevis, Escherichia coli*, Salmonella, *Staphylococcus aureus*, and *Vibrio parahaemoliticus*, obtained from the JCM, IAM, IFO, and ATCC collections.

<<PCR Assay Method>>

Sample preparation

Whole bacterial cells without extracting DNA were used as the template. In this case, were used freshly collected cells grown overnight at 35° C. in the selective medium prepared by addition of egg yolk solution to the NaCl Glycine Kim and Goepfert (NGKG) agar medium (Nissui Pharmaceutical Co.) or in the Triptosoy Agar (Eiken Kagaku). Bacterial cells, when grown in liquid media, were harvested by centrifugation and washed once with PBS buffer (pH 7.5), and appropriate counts of cells were used. About one colony of bacteria were suspended in 50 μl of sterile water and heat-treated at 95° C. for 10 minutes.

PCR amplification conditions

PCR assay was performed in the DNA Thermal Cycler (Perkin Elmer). To 5 μl of the above-mentioned heat-treated cell suspension, was added 10 μl of the reaction medium (Tris-HCl 100 mM, $MgCl_2$ 15 mM, KCl 500 mM, pH 8.3; expressed in final concentrations). This mixture contained 100 ng or more of genomic DNA, 200 μM of dNTP, and 1 μM of the primer. A cycle consisting of DNA denaturation at 94° C. for 60 seconds, annealing at 58° C. for 60 seconds, and DNA extension at 72° C. for 120 seconds was repeated 30 times.

Detection of PCR products

Following amplification, detection was carried out with gel electrophoresis. Twelve microliter of a PCR sample was applied onto the agarose gel (3% agarose, Nusieve GTG Agarose, FMC Bioproducts, Rockland). DNA bands were detected by 10 minutes staining with the ethidium bromide solution followed by UV irradiation.

The results are summarized in Table 1.

In Table 1, the abbreviations in the column 'Strain number' stand for the following organizations for deposit of the strains:

ATCC: American Type Culture Collection
JCM: Japan Collection of Microorganisms
IFO: Institute for Fermentation, Osaka
IAM: Institute of Applied Microbiology

TABLE 1

| S. no. | Microbes | Strain number | 1.2 kb gyrB | 365 bp gyrB |
|---|---|---|---|---|
| 1 | Bacillus cereus | JCM 2152 | + | + |
| 2 | Bacillus cereus | IFO 3132 | + | + |
| 3 | Bacillus cereus | IFO 3457 | + | + |
| 4 | Bacillus cereus | IFO 3836 | + | + |
| 5 | Bacillus cereus | IFO 13494 | + | + |
| 6 | Bacillus cereus | IAM 1029 | + | + |
| 7 | Bacillus cereus | IAM 1110 | + | + |
| 8 | Bacillus cereus | IAM 1229 | + | + |
| 9 | Bacillus cereus | IAM 1656 | + | + |
| 10 | Bacillus cereus | IAM 1729 | + | + |
| 11 | Bacillus cereus | IFO 3001 | + | + |
| 12 | Bacillus cereus | IFO 3131 | + | + |
| 13 | Bacillus cereus | IFO 3466 | + | + |
| 14 | Bacillus cereus | IFO 3514 | + | + |
| 15 | Bacillus cereus | IFO 3563 | + | + |
| 16 | Bacillus cereus | IFO 13597 | + | + |
| 17 | Bacillus thuringiensis | IAM 2077 | + | − |
| 18 | Bacillus anthracis | Pasteur no. 2-H | + | − |
| 19 | Bacillus mycoides | ATCC 6462 | + | − |
| 20 | Bacillus subtilis | IFO 13719 | + | − |
| 21 | Bacillus brevis | IFO 12335 | + | − |
| 22 | Esherichia coli | ATCC 25922 | + | − |
| 23 | Salmonella typhimurium | ATCC 13311 | + | − |
| 24 | Staphylococcus aureus | ATCC 12600 | + | − |
| 25 | Vibrio parahaemolyticus | ATCC 17802 | + | − |

As shown in Table 1, the amplified fragment of 365 bp was detected in all of the 15 strains of Bacillus cereus.

On the other hand, the amplified fragment was not detected in Bacillus thuringiensis, Bacillus anthracis, or Bacillus mycoides, which have biochemical properties very similar to those of Bacillus cereus. The amplified fragment could not be detected in Bacillus subtilis or Bacillus brevis either, which belongs to the same genus Bacillus as Bacillus cereus. These findings show that the primer of this invention is specific to Bacillus cereus and usable for detection of this food-borne pathogen.

Similarly, the type strains of Escherichia coli, Salmonella, Staphylococcus aureus, and Vibrio parahaemolyticus were examined for the presence of the gyrB gene and the 365 bp Bacillus cereus-specific fragment. The results are shown in Table 1. As shown in Table 1, the gyrB gene was detected but the 365 bp amplified fragment specific to Bacillus cereus could not be found in any of the strains.

Example 2

In some strains of Bacillus cereus, the 365 bp band could not be detected by electrophoresis after PCR even with the Bacillus cereus-specific primer.

For these strains, Bacillus thuringiensis- and Bacillus anthracis-specific (21 to 24 mer) primers were newly prepared by taking the gyrB gene as the index. The Bacillus thuringiensis-specific primer is an oligonucleotide having the nucleotide sequence of SEQ ID NO:9 and SEQ ID NO:10, and the Bacillus anthracis-specific primer is an oligonucleotide having the nucleotide sequence of SEQ ID NO:11 and SEQ ID NO:12. After PCR, electrophoresis followed by ethidium bromide staining revealed the band at 368 bp for Bacillus thuringiensis and the band at 245 bp for Bacillus anthracis.

The Bacillus cereus strains that could not be detected with the Bacillus cereus-specific primer were subjected to PCR with the Bacillus thuringiensis- or Bacillus anthracis-specific primer: the strains could be detected with either of the primers. Namely Bacillus cereus, Bacillus thuringiensis, and Bacillus anthracis could be differentiated on the genetic level by taking the gryB gene as the index.

Table 2 summarizes the results of PCR with the Bacillus cereus-, Bacillus thuringiensis-, or Bacillus anthracis-specific primer.

The strains tested were type strains of Bacillus cereus, Bacillus thuringiensis, Bacillus anthracis, and Bacillus mycoides and Bacillus cereus serotypes and wild strains including the strains that could not be detected with the Bacillus cereus-specific primer.

TABLE 2

| S. no. | Microbes | Strain number | B. cereus 365 bp gyrB | B. thuringiensis 368 bp gyrB | Bacillus anthracis 245 bp gyrB |
|---|---|---|---|---|---|
| 1 | Bacillus cereus | JCM 2152 | + | − | − |
| 2 | Bacillus thuringiensis | IAM 12077 | − | + | − |
| 3 | Bacillus anthracis | Pasteur no. 2-H | − | − | + |
| 4 | Bacillus mycoides | ATCC 6462 | − | − | − |
| 5 | Bacillus cereus | H1 (Serotype 1) | + | − | − |
| 6 | Bacillus cereus | H2 (Serotype 2) | + | − | − |
| 7 | Bacillus cereus | H3 (Serotype 3) | + | − | − |
| 8 | Bacillus cereus | H4 (Serotype 4) | + | − | − |
| 9 | Bacillus cereus | H5 (Serotype 5) | − | − | + |
| 10 | Bacillus cereus | H6 (Serotype 6) | − | − | + |
| 11 | Bacillus cereus | H7 (Serotype 7) | − | − | + |
| 12 | Bacillus cereus | H8 (Serotype 8) | + | − | − |
| 13 | Bacillus cereus | H9 (Serotype 9) | + | − | − |
| 14 | Bacillus cereus | H10 (Serotype 10) | + | − | − |

TABLE 2-continued

| S. no. | Microbes | Strain number | B. cereus 365 bp gyrB | B. thuringiensis 368 bp gyrB | Bacillus anthracis 245 bp gyrB |
|---|---|---|---|---|---|
| 15 | Bacillus cereus | H11 (Serotype 11) | + | − | − |
| 16 | Bacillus cereus | H12 (Serotype 12) | + | − | − |
| 17 | Bacillus cereus | H13 (Serotype 13) | + | − | − |
| 18 | Bacillus cereus | H14 (Serotype 14) | + | − | − |
| 19 | Bacillus cereus | H15 (Serotype 15) | + | − | − |
| 20 | Bacillus cereus | H16 (Serotype 16) | − | + | − |
| 21 | Bacillus cereus | H17 (Serotype 17) | − | − | + |
| 22 | Bacillus cereus | H18 (Serotype 18) | + | − | − |
| 23 | Bacillus cereus | Wild strain 126 | − | + | − |
| 24 | Bacillus cereus | Wild strain 127 | − | + | − |
| 25 | Bacillus cereus | Wild strain 139 | − | − | + |

However this classification on the genetic level is not always in agreement with the current biochemical classification. According to the biochemical classification, Bacillus cereus is different from Bacillus thuringiensis only in production of insecticidal protein; Bacillus thuringiensis produces insecticidal protein. Only Bacillus anthracis is susceptible to bacteriolysis by γ phage, which characterizes this species. When the classification on the genetic level is not always in agreement with the biochemical classification, as in the present case, the biochemical classification is preferred; even when a strain is classified as Bacillus anthracis on the genetic level, the strain is not necessarily the highly pathogenic strain of Bacillus anthracis.

The so-called Bacillus cereus group includes Bacillus thuringiensis, Bacillus anthracis, and Bacillus mycoides, in addition to Bacillus cereus. In view of hazard to man and cattle, Bacillus cereus, Bacillus thuringiensis, and Bacillus anthracis are unfavorable bacteria because of their production of toxin. Bacillus mycoides does not produce such toxin and may be separated from the former 3 species from the viewpoint of safety. Therefore it may be very meaningful that Bacillus cereus, Bacillus thuringiensis, and Bacillus anthracis can be detected as mentioned above.

EFFECT OF THE INVENTION

Primers that can react specifically with the gyrB gene of Bacillus cereus, Bacillus thuringiensis, and Bacillus anthracis to enable identification of these bacteria by differentiation from bacteria of other Bacillus species or of genera other than the genus Bacillus could be provided. Bacillus cereus-specific gyrB gene fragments of 365 bp, 368 bp, and 245 bp can be detected from bacterial cells with the PCR method without DNA extraction, by using the Bacillus cereus-specific primer for Bacillus cereus, with the Bacillus thuringiensis-specific primer for Bacillus thuringiensis, and with the Bacillus anthracis-specific primer for Bacillus anthracis, respectively. Bacillus cereus in a sample can be detected by differentiation on the genetic level from Bacillus thuringiensis and Bacillus anthracis.

What is claimed is:

1. An oligonucleotide selected from the group consisting of an oligonucleotide (A) comprising a nucleotide segment which specifically hybridizes to and specifically amplifies the gyrase sub-unit B (gyrB) gene sequence of SEQ ID NO:1, an oligonucleotide (B) comprising a nucleotide segment which specifically hybridizes to and specifically amplifies the gyrase sub-unit B (gyrB) gene sequence of SEQ ID NO:3, and an oligonucleotide (C) comprising a nucleotide segment which specifically hybridizes to and specifically amplifies the gyrase sub-unit B (gyrB) gene sequence of SEQ ID NO:5.

2. The oligonucleotide of claim 1, wherein said oligonucleotide (A) does not contain any of (i) a nucleotide segment which specifically hybridizes to and specifically amplifies the gyrase sub-unit B (gyrB) gene sequence of SEQ ID NO:3 and (ii) a nucleotide segment which specifically hybridizes to and specifically amplifies the gyrase sub-unit B (gyrB) gene sequence of SEQ ID NO:5, said oligonucleotide (B) does not contain any of (i) a nucleotide segment which specifically hybridizes to and specifically amplifies the gyrase sub-unit B (gyrB) gene sequence of SEQ ID NO:1 and (ii) a nucleotide segment which specifically hybridizes to and specifically amplifies the gyrase sub-unit B (gyrB) gene sequence of SEQ ID NO:5, and said oligonucleotide (C) does not contain any of (i) a nucleotide segment which specifically hybridizes to and specifically amplifies the gyrase sub-unit B (gyrB) gene sequence of SEQ ID NO:1 and (ii) a nucleotide segment which specifically hybridizes to and specifically amplifies the gyrase sub-unit B (gyrB) gene sequence of SEQ ID NO:3.

3. An oligonucleotide selected from the group consisting of an oligonucleotide (A) comprising a nucleotide segment which specifically hybridizes to and specifically amplifies the gyrase sub-unit B (gyrB) gene sequence of SEQ ID NO:1 and containing the nucleotide sequence of SEQ ID NO:7 or SEQ ID NO:8, an oligonucleotide (B) comprising a nucleotide segment which specifically hybridizes to and specifically amplifies the gyrase (gyrB) gene sequence of SEQ ID NO:3 and containing the nucleotide sequence of SEQ ID NO:9 or SEQ ID NO:10, and an oligonucleotide (C) comprising a nucleotide segment which specifically hybridizes to and specifically amplifies the gyrase sub-unit B (gyrB) gene sequence of SEQ ID NO:5 and containing the nucleotide sequence of SEQ ID NO:11 or SEQ ID NO:12.

4. A primer set selected from the group consisting of:

a primer set comprising an oligonucleotide (A) comprising a nucleotide segment which specifically hybridizes to and specifically amplifies the gyrase sub-unit B (gyrB) gene sequence of SEQ ID NO:1, said primer set consisting of an oligonucleotide ($a_1$) containing the nucleotide sequence of SEQ ID NO:7 and an oligonucleotide ($a_2$) containing the nucleotide sequence of SEQ ID NO:8, a primer set comprising an oligonucleotide (B) comprising a nucleotide segment which specifically hybridizes to and specifically amplifies the gyrase sub-unit B (gyrB) gene sequence of SEQ ID NO:3, said primer set consisting an oligonucleotide ($b_1$) containing the nucleotide sequence of SEQ ID NO:9 and an oligonucleotide ($b_2$) containing the nucleotide sequence of SEQ. ID NO:10, and a primer set comprising an oligonucleotide (C) comprising a nucleotide segment which specifically hybridizes to and specifically amplifies the gyrase sub-unit B (gyrB) gene sequence of SEQ ID NO:5, said primer set consisting of an oligonucleotide ($c_1$) containing the nucleotide sequence of SEQ ID NO:11 and an oligonucleotide ($c_2$) containing the nucleotide sequence of SEQ ID NO: 12.

5. A method of detecting in a sample a target DNA comprising any of the gyrase sub-unit B (gyrB) gene sequences of SEQ ID NO:1, SEQ ID NO:3 and SEQ ID NO:5, comprising:

(i) amplifying said target DNA using a group of oligonucleotides comprising:

at least one oligonucleotide (A) comprising a nucleotide segment which specifically hybridizes to and specifically amplifies the gyrase sub-unit B (gyrB) gene sequence of SEQ ID NO:1, (b) at least one oligonucleotide (B) comprising a nucleotide segment which specifically hybridizes to and specifically amplifies the gyrase sub-unit B (gyrB) gene sequence of SEQ ID NO:3, and (c) at least one oligonucleotide (C) comprising a nucleotide segment which specifically hybridizes to and specifically amplifies the gyrase sub-unit B (gyrB) gene sequence of SEQ ID NO:5, wherein said oligonucleotides (A), (B), and (C) prime synthesis of the gyrase sub-unit B (gyrB) gene sequences of SEQ ID NO: 1, SEQ ID NO: 3, and SEQ ID NO: 5, respectively, and (ii) detecting the presence or absence of amplification products produced in step (i), wherein the presence of said amplification products is indicative of the presence of a target DNA comprising any of the gyrase sub-unit B (gyrB) gene sequences of SEQ ID NO:1, SEQ ID NO:3, and SEQ ID NO:5.

6. The method of claim 5 wherein said group of oligonucleotides comprises a group of primer sets comprising:

a first primer set consisting of two different oligonucleotides (A), a second primer set consisting of two different oligonucleotides (B), and a third primer set consisting of two different oligonucleotides (C).

7. The method of claim 6, wherein:

said first primer set consists of an oligonucleotide ($a_1$) containing the nucleotide sequence of SEQ ID NO: 7 and an oligonucleotide ($a_2$) containing the nucleotide sequence of SEQ ID NO: 8, said second primer set consists of an oligonucleotide ($b_1$) containing the nucleotide sequence of SEQ ID NO: 9 and an oligonucleotide ($b_2$) containing the nucleotide sequence of SEQ ID NO: 10, and said third primer set consists of an oligonucleotide ($c_1$) containing the nucleotide sequence of SEQ ID NO: 11 and an oligonucleotide ($c_2$) containing the nucleotide sequence of SEQ ID NO: 12.

8. A method of detecting in a sample a target DNA comprising the gyrase sub-unit B (gyrB) gene sequence of SEQ ID NO:1, comprising:

(i) amplifying said target DNA using at least one oligonucleotide (A) comprising a nucleotide segment which specifically hybridizes to and specifically amplifies the gyrase sub-unit B (gyrB) gene sequence of SEQ ID NO:1 to prime synthesis of the gyrase sub-unit B (gyrB) gene sequence of SEQ ID NO:1, and (ii) detecting the presence or absence of amplification products produced in step (i), wherein the presence of said amplification products is indicative of the presence of a target DNA comprising the gyrase sub-unit B (gyrB) gene sequence of SEQ ID NO:1.

9. A method of detecting in a sample a target DNA comprising the gyrate sub-unit B (gyrB) gene sequence of SEQ ID NO:3, comprising:

(i) amplifying said target DNA using at least an oligonucleotide (B) comprising a nucleotide segment which specifically hybridizes to and specifically amplifies the gyrase sub-unit B (gyrB) gene sequence of SEQ ID NO:3 to prime synthesis of the gyrase sub-unit B (gyrB) gene sequence of SEQ I]D NO:3, and (ii) detecting the presence or absence of amplification products produced in step (i), wherein the presence of said amplification products is indicative of the presence of a target DNA comprising the gyrase sub-unit B (gyrB) gene sequence of SEQ ID NO:3.

10. A method of detecting in a sample a target DNA comprising the gyrase sub-unit B (gyrB) gene sequence of SEQ ID NO:5, comprising:

(i) amplifying said target DNA using at least one oligonucleotide (C) comprising a nucleotide segment which specifically hybridizes to and specifically amplifies the gyrase sub-unit B (gyrB) gene sequence of SEQ ID) NO:5 to prime synthesis of the gyrase sub-unit B (gyrB) gene sequence of SEQ ID NO:5, and (ii) detecting the presence or absence of amplification products produced in step (i), wherein the presence of said amplification products is indicative of the presence of a target DNA comprising the gyrase sub-unit B (gyrB) gene sequence of SEQ ID NO:5.

11. The method of claim 8, wherein two oligonucleotides (A) are employed, and wherein said oligonucleotides (A) consist of a primer set consisting of two different oligonucleotides (A).

12. The method of claim 9 wherein two oligonucleotides (B) are employed, and wherein said oligonucleotides (B) consist of a primer set consisting of two different oligonucleotides (B).

13. The method of claim 10 wherein two oligonucleotides (C) are employed, and wherein said oligonucleotides (C) consist of a primer set consisting of two different oligonucleotides (C).

14. The method of claim 11 wherein said primer set consists of an oligonucleotide ($a_1$) containing the nucleotide sequence of SEQ ID NO: 7 and an oligonucleotide ($a_2$) containing the nucleotide sequence of SEQ ID NO: 8.

15. The method of claim 12 wherein said primer set consists of an oligonucleotide ($b_1$) containing the nucleotide sequence of SEQ ID NO: 9 and an oligonucleotide ($b_2$) containing the nucleotide sequence of SEQ ID NO: 10.

16. The method of claim 13 wherein said primer set consists of an oligonucleotide ($c_1$) containing the nucleotide sequence of SEQ ID NO: 11 and an oligonucleotide ($c_2$) containing the nucleotide sequence of SEQ ID NO: 12.

\* \* \* \* \*

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 1212 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
CATGCAGGAG GCAAATTTGA CGGTGGCGGT TATAAAGTTT CTGGTGGTTT ACATGGTGTT      60

GGGGCATCGG TTGTAAATGC TCTATCAACA GAATTAGAAG TATTTGTACA TCGTGAAGGT     120

AAAATCCATT ACCAAAAATA CGAAAGAGGT ATTCCGGTTG CGGATTTAAA AGTCATTGGT     180

GACACCGATC AAACAGGAAC AATAACTCGA TTTAAACCAG ATCCGGAAAT TTTCCAAGAA     240

ACAACAGTAT ACGATTTTGA TACGCTAGCA ACTCGTATGC GTGAATTAGC GTTTTTAAAT     300

CGTAATATTA AATTAACAAT TGAAGATAAA CGTGAACGTA AGCAAAAGAA AGAATTCCAT     360
```

```
TACGAAGGTG GAATTAAATC ATACGTTGAG CATTTAAATC GCTCAAAACA ACCGATTCAT      420

GAAGAGCCTG TGTACGTAGA AGGTTCAAAA GATGGTATTC AGGTTGAGGT TTCTCTTCAA      480

TATAACGAAG GATACACAAA TAATATTTAC TCATTTACGA ATAACATCCA TACGTATGAA      540

GGTGGTACAC ATGAGGTAGG TTTTAAAACA GCTTTAACTC GTGTAATCAA CGACTATGGT     600

CGTAAAAATA GCATTTTAAA AGATGCGGAC AGTAATTTAA CTGGTGAGGA TGTTCGTGAA      660

GGTTTAACAG CAATTGTATC AATCAAGCAT CCAAATCCAC AATTTGAAGG ACAAACGAAG     720

ACAAAACTTG GGAATAGTGA AGCGAGAACA ATTACAGAGT CTGTATTCTC AGAGGCATTT     780

GAAAAGTTCT TACTAGAAAA TCCTAATGTA GCGCGAAAAA TTGTAGAAAA AGGTACGATG     840

GCTGCACGTG CACGTGTAGC TGCGAAAAAA GCGCGTGAAT TGACACGTCG AAAGAGTGCG     900

TTAGAAGTTT CAAGTTTACC TGGTAAATTA GCTGATTGCT CTTCGAAAGA TCCAGCAATT     960

AGTGAAATTT ACATCGTAGA GGGTGACTCT GCGGGTGGAT CTGCAAAACA AGGACGCGAT    1020

CGTCATTTCC AAGCAATTTT ACCGCTGAAG GGTAAAATTA TTAATGTGGA AAAGGCGCGC    1080

TTAGATAAGA TTTTATCAAA TGATGAAGTT CGTACAATTA TTACGGCAAT CGGTACAAAT    1140

ATTGGTGGAG ACTTCGATAT TGAAAAAGCA CGCTATCATA AAGTTATTAT CATGACAGAT    1200

GCAGACGTGG AC                                                       1212

(2) INFORMATION FOR SEQ ID NO:2:

(i) SEQUENCE CHARACTERISTICS:
        (A) LENGTH: 404 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

His Ala Gly Gly Lys Phe Asp Gly Gly Tyr Lys Val Ser Gly Gly
 1               5                  10                  15

Leu His Gly Val Gly Ala Ser Val Val Asn Ala Leu Ser Thr Glu Leu
                20                  25                  30

Glu Val Phe Val His Arg Glu Gly Lys Ile His Tyr Gln Lys Tyr Glu
                35                  40                  45

Arg Gly Ile Pro Val Ala Asp Leu Lys Val Ile Gly Asp Thr Asp Gln
    50                  55                  60

Thr Gly Thr Ile Thr Arg Phe Lys Pro Asp Pro Glu Ile Phe Gln Glu
65                  70                  75                  80

Thr Thr Val Tyr Asp Phe Asp Thr Leu Ala Thr Arg Met Arg Glu Leu
                85                  90                  95

Ala Phe Leu Asn Arg Asn Ile Lys Leu Thr Ile Glu Asp Lys Arg Glu
                100                 105                 110

Arg Lys Gln Lys Lys Glu Phe His Tyr Glu Gly Gly Ile Lys Ser Tyr
    115                 120                 125

Val Glu His Leu Asn Arg Ser Lys Gln Pro Ile His Glu Glu Pro Val
    130                 135                 140

Tyr Val Glu Gly Ser Lys Asp Gly Ile Gln Val Glu Val Ser Leu Gln
145                 150                 155                 160

Tyr Asn Glu Gly Tyr Thr Asn Asn Ile Tyr Ser Phe Thr Asn Asn Ile
                165                 170                 175

His Thr Tyr Glu Gly Gly Thr His Glu Val Gly Phe Lys Thr Ala Leu
                180                 185                 190
```

-continued

```
Thr Arg Val Ile Asn Asp Tyr Gly Arg Lys Asn Ser Ile Leu Lys Asp
        195                 200                 205

Ala Asp Ser Asn Leu Thr Gly Glu Asp Val Arg Glu Gly Leu Thr Ala
    210                 215                 220

Ile Val Ser Ile Lys His Pro Asn Pro Gln Phe Glu Gly Gln Thr Lys
225                 230                 235                 240

Thr Lys Leu Gly Asn Ser Glu Ala Arg Thr Ile Thr Glu Ser Val Phe
                245                 250                 255

Ser Glu Ala Phe Glu Lys Phe Leu Leu Glu Asn Pro Asn Val Ala Arg
                260                 265                 270

Lys Ile Val Glu Lys Gly Thr Met Ala Ala Arg Ala Arg Val Ala Ala
            275                 280                 285

Lys Lys Ala Arg Glu Leu Thr Arg Arg Lys Ser Ala Leu Glu Val Ser
        290                 295                 300

Ser Leu Pro Gly Lys Leu Ala Asp Cys Ser Ser Lys Asp Pro Ala Ile
305                 310                 315                 320

Ser Glu Ile Tyr Ile Val Glu Gly Asp Ser Ala Gly Gly Ser Ala Lys
                325                 330                 335

Gln Gly Arg Asp Arg His Phe Gln Ala Ile Leu Pro Leu Lys Gly Lys
                340                 345                 350

Ile Ile Asn Val Glu Lys Ala Arg Leu Asp Lys Ile Leu Ser Asn Asp
            355                 360                 365

Glu Val Arg Thr Ile Ile Thr Ala Ile Gly Thr Asn Ile Gly Gly Asp
        370                 375                 380

Phe Asp Ile Glu Lys Ala Arg Tyr His Lys Val Ile Ile Met Thr Asp
385                 390                 395                 400

Ala Asp Val Asp
```

(2) INFORMATION FOR SEQ ID NO:3:

(i) SEQUENCE CHARACTERISTICS:
        (A) LENGTH: 1212 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
CATGCTGGTG GGAAATTCGA CGGTGGCGGT TATAAAGTTT CTGGTGGTTT GCACGGTGTT      60

GGTGCATCTG TTGTAAATGC CTTATCAACA GAATTAGAAG TATTTGTACA TCGTGATGGC     120

AAAATCCATT ACCAAAAATA CCAAAGAGGT ATTCCGGTTG CAGATTTAAA AGTCATCGGT     180

GATACAGATA AGACTGGAAC AATAACTCGC TTTAAACCGG ATCCAGAAAT TTTTAAAGAG     240

ACGACAGAAT ATGAATTCGA TACGCTCGCG ACTCGTGTGC GTGAGTTGGC GTTTTTAAAT     300

CGTAATATTA AATTAACAAT TGAAGATAAA CGTGAACATA AGCAAAAGAA AGAGTTCCAC     360

TATGAAGGTG GAATTAAATC ATATGTTGAA CATTTAAATC GTTCAAAACA ACCAATTCAT     420

GAAGAGCCTG TATATGTAGA AGGTTCAAAA GATGGTATTC AAGTTGAAGT TGCGCTTCAA     480

TATAACGAAG GATATACAAA TCATATTTAC TCATTTACAA ATAATATTCA TACGTATGAA     540

GGTGGTACAC ATGAGGTAGG ATTTAAAACT GCCTTAACAC GTGTTATTAA CGATTATGGT     600

CGTAAAAATA ACATTTTAAA AGATGCGGAT AGTAATTTGA CTGGTGAAGA TGTTCGTGAA     660

GGTTTAACAG CAATCGTGTC AATTAAACAT CCAAATCCAC AATTTGAAGG CAAACGAAG      720

ACGAAACTTG GAAATAGTGA AGCGAGAACG ATTACGGAGT CAGTATTCTC TGAGGCTTTT     780
```

-continued

```
GAAAAATTCT TACTGGAAAA TCCCAATGTT GCACGTAAGG TTGTAGATAA AGGGACGATG      840

GCAGCACGTG CGCGTGTAGC AGCTAAAAAG GCTCGTGAGC TAACTCGCCG AAAGAGTGCT      900

TTAGAAGTTT CAAGTTTACC AGGGAAATTG GCAGATTGTT CTTCTAAAGA TCCAGCAATT      960

AGTGAAATTT ATATCGTAGA GGGTGACTCT GCGGGTGGAT CTGCAAAACA AGGACGCGAT     1020

CGTCATTTTC AAGCAATTTT ACCGCTGAAG GGTAAAATTA TTAATGTTGA AAAGGCACGC     1080

TTAGATAAGA TTTTATCAAA TGATGAAGTT CGTACAATTA TTACGGCGAT TGGTACAAAT     1140

ATTGGTGGGG ACTTCGATAT CGAAAAAGCA CGCTATCATA AAGTTATTAT TATGACCGAC     1200

GCCGACGTTG AT                                                        1212
```

(2) INFORMATION FOR SEQ ID NO:4:

(i) SEQUENCE CHARACTERISTICS:
        (A) LENGTH: 404 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

```
His Ala Gly Gly Lys Phe Asp Gly Gly Gly Tyr Lys Val Ser Gly Gly
 1               5                  10                  15

Leu His Gly Val Gly Ala Ser Val Val Asn Ala Leu Ser Thr Glu Leu
            20                  25                  30

Glu Val Phe Val His Arg Asp Gly Lys Ile His Tyr Gln Lys Tyr Gln
        35                  40                  45

Arg Gly Ile Pro Val Ala Asp Leu Lys Val Ile Gly Asp Thr Asp Lys
    50                  55                  60

Thr Gly Thr Ile Thr Arg Phe Lys Pro Asp Pro Glu Ile Phe Lys Glu
65                  70                  75                  80

Thr Thr Glu Tyr Glu Phe Asp Thr Leu Ala Thr Arg Val Arg Glu Leu
                85                  90                  95

Ala Phe Leu Asn Arg Asn Ile Lys Leu Thr Ile Glu Asp Lys Arg Glu
            100                 105                 110

His Lys Gln Lys Lys Glu Phe His Tyr Glu Gly Gly Ile Lys Ser Tyr
        115                 120                 125

Val Glu His Leu Asn Arg Ser Lys Gln Pro Ile His Glu Glu Pro Val
    130                 135                 140

Tyr Val Glu Gly Ser Lys Asp Gly Ile Gln Val Glu Val Ala Leu Gln
145                 150                 155                 160

Tyr Asn Glu Gly Tyr Thr Asn His Ile Tyr Ser Phe Thr Asn Asn Ile
                165                 170                 175

His Thr Tyr Glu Gly Gly Thr His Glu Val Gly Phe Lys Thr Ala Leu
            180                 185                 190

Thr Arg Val Ile Asn Asp Tyr Gly Arg Lys Asn Asn Ile Leu Lys Asp
        195                 200                 205

Ala Asp Ser Asn Leu Thr Gly Glu Asp Val Arg Glu Gly Leu Thr Ala
    210                 215                 220

Ile Val Ser Ile Lys His Pro Asn Pro Gln Phe Glu Gly Gln Thr Lys
225                 230                 235                 240

Thr Lys Leu Gly Asn Ser Glu Ala Arg Thr Ile Thr Glu Ser Val Phe
                245                 250                 255

Ser Glu Ala Phe Glu Lys Phe Leu Leu Glu Asn Pro Asn Val Ala Arg
```

```
                260                  265                  270
Lys Val Asp Lys Gly Thr Met Ala Ala Arg Ala Arg Val Ala Ala
                275                  280                  285
Lys Lys Ala Arg Glu Leu Thr Arg Arg Lys Ser Ala Leu Glu Val Ser
    290                  295                  300
Ser Leu Pro Gly Lys Leu Ala Asp Cys Ser Ser Lys Asp Pro Ala Ile
305                  310                  315                  320
Ser Glu Ile Tyr Ile Val Glu Gly Asp Ser Ala Gly Gly Ser Ala Lys
                325                  330                  335
Gln Gly Arg Asp Arg His Phe Gln Ala Ile Leu Pro Leu Lys Gly Lys
                340                  345                  350
Ile Ile Asn Val Glu Lys Ala Arg Leu Asp Lys Ile Leu Ser Asn Asp
                355                  360                  365
Glu Val Arg Thr Ile Ile Thr Ala Ile Gly Thr Asn Ile Gly Gly Asp
                370                  375                  380
Phe Asp Ile Glu Lys Ala Arg Tyr His Lys Val Ile Ile Met Thr Asp
385                  390                  395                  400
Ala Asp Val Asp
```

(2) INFORMATION FOR SEQ ID NO:5:

(i) SEQUENCE CHARACTERISTICS:
        (A) LENGTH: 1212 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
CATGCTGGGG GAAAATTTGA CGGCGGCGGT TATAAAGTTT CTGGTGGTTT GCATGGTGTT     60

GGGGCATCTG TAGTAAATGC TCTATCAACA GAACTAGAGG TATTTGTACA TCGTGAAGGT    120

AAAATCCATT ATCAAAAATA CGAAAGAGGT ATTCCGGTTG CGGATTTAAA AGTCATTGGT    180

GATACAGATC AAACGGGAAC GATAACTCGA TTTAAACCAG ATCCAGAAAT TTTTCAGGAA    240

ACAACAGTAT ACGAATTTGA TACACTAGCA ACTCGTATGC GTGAATTAGC ATTTTTAAAT    300

CGTAATATTA AACTGACGAT TGAAGATAAA CGTGAACATA AGCAAAAAAA AGAATTCCAT    360

TGTGAAGGTG GAATTAAATC ATATGTTGAG CATTTAAACC GCTCAAAACA ACCAATCCAT    420

GAAGAGCCTG TATATGTAGA AGGATCAAAA GATGGTATTC AAGTTGAAGT TTCCTTACAG    480

TATAACGAAG GATATACAAA TAATATTTAC TCATTTACGA ACAACATTCA CACGTATGAA    540

GGTGGAACAC ATGAAGTAGG GTTTAAAACA GCTTTAACTC GTGTGATTAA CGATTATGGG    600

CGTAAAAATA GTATTCTAAA AGATGCAGAC AGTAATTTAA CTGGTGAGGA CGTTCGTGAA    660

GGTTTAACTG CAATTGTATC AATTAAACAT CCAGATCCAC AATTTGAAGG ACAAACGAAG    720

ACGAAACTTG GGAATAGTGA AGCGAGAACG ATTACAGAGT CTGTGTTTTC AGAGGCATTT    780

GAAAAGTTCT TACTAGAAAA CCCGAACGTT GCACGAAAAA TCGTAGAAAA AGGTACGATG    840

GCAGCGCGTG CACGTGTTGC AGCGAAAAAA GCACGTGAAT TGACACGTCG TAAGAGCGCG    900

TTAGAAGTTT CAAGTTTACC TGGTAGATTA GCAGATTGCT CTTCAAAAGA TCCAGCAATT    960

AGTGAAATTT ACATTGTAGA GGGTGACTCT GCCGGTGGAT CAGCAAAGCA AGGGCGTGAT   1020

CGTCACTTCC AAGCGATTTT ACCACTGAAA GGTAAAATTA TTAACGTTGA AAAGGCAAGA   1080

TTAGATAAAA TCTTATCTAA CGATGAAGTG CGTACAATTA TTACTGCAAT TGGTACGAAC   1140
```

```
ATTGGCGGAG ATTTTGATAT TGAGAAAGCT CGTTATCATA AAGTTATTAT TATGACGGAT      1200

GCCGACGTCG AC                                                          1212
```

(2) INFORMATION FOR SEQ ID NO:6:

(i) SEQUENCE CHARACTERISTICS:
        (A) LENGTH: 404 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
His Ala Gly Gly Lys Phe Asp Gly Gly Tyr Lys Val Ser Gly Gly
1               5                   10                  15

Leu His Gly Val Gly Ala Ser Val Val Asn Ala Leu Ser Thr Glu Leu
                20                  25                  30

Glu Val Phe Val His Arg Glu Gly Lys Ile His Tyr Gln Lys Tyr Glu
            35                  40                  45

Arg Gly Ile Pro Val Ala Asp Leu Lys Val Ile Gly Asp Thr Asp Gln
50                  55                  60

Thr Gly Thr Ile Thr Arg Phe Lys Pro Asp Pro Glu Ile Phe Gln Glu
65                  70                  75                  80

Thr Thr Val Tyr Glu Phe Asp Thr Leu Ala Thr Arg Met Arg Glu Leu
                85                  90                  95

Ala Phe Leu Asn Arg Asn Ile Lys Leu Thr Ile Glu Asp Lys Arg Glu
                100                 105                 110

His Lys Gln Lys Lys Glu Phe His Cys Glu Gly Gly Ile Lys Ser Tyr
            115                 120                 125

Val Glu His Leu Asn Arg Ser Lys Gln Pro Ile His Glu Glu Pro Val
130                 135                 140

Tyr Val Glu Gly Ser Lys Asp Gly Ile Gln Val Glu Val Ser Leu Gln
145                 150                 155                 160

Tyr Asn Glu Gly Tyr Thr Asn Asn Ile Tyr Ser Phe Thr Asn Asn Ile
                165                 170                 175

His Thr Tyr Glu Gly Gly Thr His Glu Val Gly Phe Lys Thr Ala Leu
                180                 185                 190

Thr Arg Val Ile Asn Asp Tyr Gly Arg Lys Asn Ser Ile Leu Lys Asp
            195                 200                 205

Ala Asp Ser Asn Leu Thr Gly Glu Asp Val Arg Glu Gly Leu Thr Ala
210                 215                 220

Ile Val Ser Ile Lys His Pro Asp Pro Gln Phe Glu Gly Gln Thr Lys
225                 230                 235                 240

Thr Lys Leu Gly Asn Ser Glu Ala Arg Thr Ile Thr Glu Ser Val Phe
                245                 250                 255

Ser Glu Ala Phe Glu Lys Phe Leu Leu Glu Asn Pro Asn Val Ala Arg
                260                 265                 270

Lys Ile Val Glu Lys Gly Thr Met Ala Ala Arg Ala Val Ala Ala
            275                 280                 285

Lys Lys Ala Arg Glu Leu Thr Arg Arg Lys Ser Ala Leu Glu Val Ser
290                 295                 300

Ser Leu Pro Gly Arg Leu Ala Asp Cys Ser Ser Lys Asp Pro Ala Ile
305                 310                 315                 320

Ser Glu Ile Tyr Ile Val Glu Gly Asp Ser Ala Gly Gly Ser Ala Lys
                325                 330                 335
```

```
Gln Gly Arg Asp Arg His Phe Gln Ala Ile Leu Pro Leu Lys Gly Lys
            340                 345                 350

Ile Ile Asn Val Glu Lys Ala Arg Leu Asp Lys Ile Leu Ser Asn Asp
        355                 360                 365

Glu Val Arg Thr Ile Ile Thr Ala Ile Gly Thr Asn Ile Gly Gly Asp
    370                 375                 380

Phe Asp Ile Glu Lys Ala Arg Tyr His Lys Val Ile Ile Met Thr Asp
385                 390                 395                 400

Ala Asp Val Asp
```

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

ATTGGTGACA CCGATCAAAC A                                      21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

TCATACGTAT GGATGTTATT C                                      21

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

ATCGGTGATA CAGATAAGAC T                                      21

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CCTTCATACG TATGAATATT ATTT                                  24

(2) INFORMATION FOR SEQ ID NO:11:

(i) SEQUENCE CHARACTERISTICS:

-continued (A) LENGTH: 21 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:11:

AATCGTAATA TTAAACTGAC G                                          21

(2) INFORMATION FOR SEQ ID NO:12:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:12:

CCTTCATACG TGTGAATGTT G                                          21